United States Patent [19]

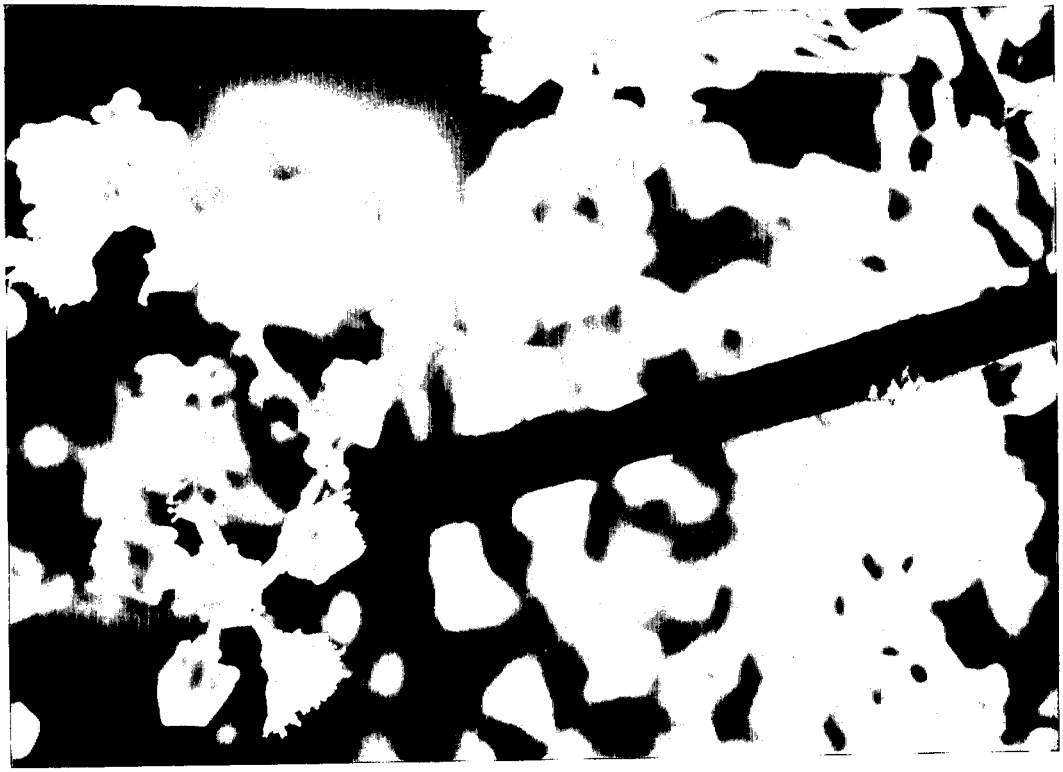
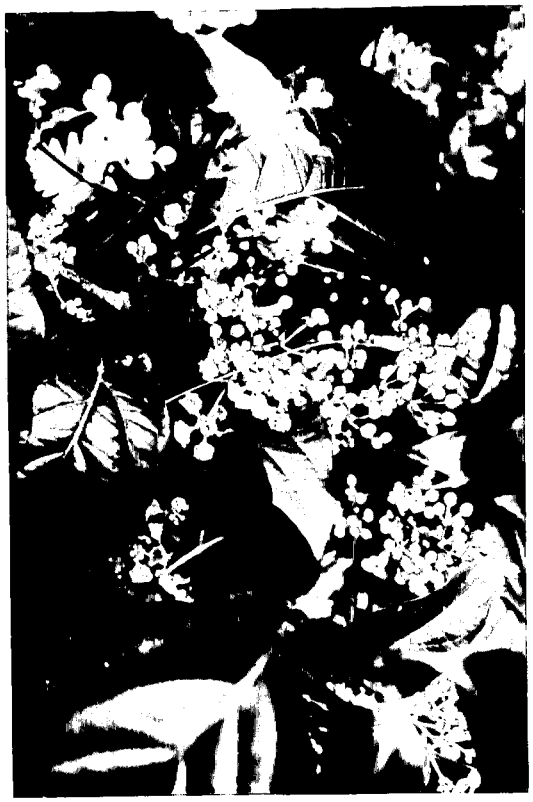
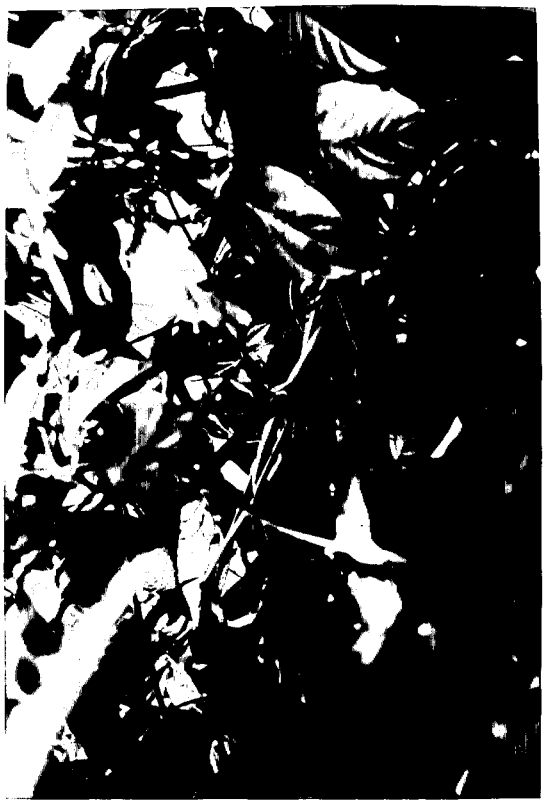

Miller

[11] Patent Number: Plant 5,751

[45] Date of Patent: Jun. 17, 1986

[54] *BANISTERIOPSIS CAAPI* (cv) 'DA VINE'

[76] Inventor: Loren S. Miller, 1788 Oak Creek Dr., Apt. 407, Palo Alto, Calif. 94303

[21] Appl. No.: 669,745

[22] Filed: Nov. 7, 1984

Related U.S. Application Data

[63] Continuation of Ser. No. 266,114, May 21, 1981, abandoned.

[51] Int. Cl.[4] ..... A01H 5/00
[52] U.S. Cl. ..... Plt./54
[58] Field of Search ..... Plt./54

[56] References Cited

U.S. PATENT DOCUMENTS

P.P. 3,008 12/1970 Magnuson ..... Plt./88
P.P. 4,253 5/1978 Arnold ..... Plt./88

OTHER PUBLICATIONS

Gates, Bronwen *Flora Neotropica* Monograph No. 30, Banisteriopsis, Diplopterys (Malpighiaceae) Published for Organization for Neotropica by the New York Botanical Garden, N.Y. Feb. 18, 1982.

*Primary Examiner*—James R. Feyrer

[57] ABSTRACT

A new and distinct *Banisteriopsis caapi* plant named 'Da Vine' which is particularly characterized by the rose color of its flower petals which fade with age to near white, and its medicinal properties.

2 Drawing Figures

CROSS-REFERENCE TO RELATED APPLICATIONS

This application is a continuation application of application Ser. No. 266,114, filed on May 21, 1981 now abandoned.

BACKGROUND OF THE INVENTION

The invention relates to a new and distinct variety (cultivar) of the species *Banisteriopsis caapi.* The plant was discovered by and caused to be asexually reproduced from cuttings by applicant. All asexual reproductions of the plant show that the plant is stable, being true to the form to the discovered plant in all distinguishing respects.

The new plant is named 'Da Vine'. This plant was discovered growing in a domestic garden in the Amazon rain-forest of South America. The instant plant presents flower petals which are rose colored fading to white with age. The instant plant may be distinguished from the species per se in flower color, *B. caapi* having pale pink flowers fading to pale yellow.

SUMMARY OF THE INVENTION

The instant plant may be particularly distinguished from typical forms of *B. caapi* by the following list of outstanding characteristics:

1. Leaves of different sizes, shapes, and texture. (see chart)
2. 'Da Vine' has different size pedicels than are typical for *B. cappi.* (see chart)
3 The instant plant is more pubescent than is seen in the species. (see chart)
4. In flower petal color and size. (see chart)
5. 'Da Vine' has no samaras. (nut)

The subject plant is being investigated for its medicinal value in cancer treatment and psycho-therapy. It is useful in treating post-encephalytic Parkinsonism and angina pectoris. It also has antiseptic, bactericidal properties and has both amoebicidal and antihelmentic action. It is an attractive house plant which seasonally blooms.

BRIEF DESCRIPTION OF THE DRAWING

FIG. 1 shows the flower parts of the novel plant at various stages after opening and while attached to a vine.

FIG. 2 depicts foliage.

FIG. 3 shows the vine habit of the plant.

BOTANICAL DESCRIPTION OF PLANT

The following botanical description of the plant is based on observation of a mature specimen growing at Harold Lyon Arboreteum, Oahu, Hi., under semi-tropical, outside conditions. Color specifications of the flower petals are in accordance with *Color Standards and Color Nomenclature* by R. Ridgway, 1912. Other color descriptions are in accordance with: Dictionary of Colour Standards, 1951 British Colour Council 10a Chandes St., London. Horticultural Colour Chart, Vol. I, 1939 British Colour Council, Wilson Colour, Ltd. Horticultural Colour Chart, Vol. II, 1941 British Colour Council, Wilson Colour, Ltd.

Name: *Banisteriopsis caapi* (cv) 'Da Vine'.

Parentage: Unknown, apparently a chance seedling.

Plant type: Tropical perennial flowering vine, an understory plant in jungles in the Amazon basin in the wild. Houseplant.

Tenderness:

*Cold, hardiness.*—Unknown.

*Sensitivity to light.*—Unknown.

Vigor: Growth rate: unknown because we constantly prune the vine. However, it is definitely a fast growing plant with a growth rate of at least 5–10 m per year, when young.

Habit: Woody vine (liana) tropical perennial, shrub, small tree.

Branching: Opposite branching.

Stems:

*Color.*—Young stem — Emerald Green 758 (Hort. Colour Chart). Old Stem — Spinach Green 960 (Hort. Colour Chart). Bark — Mink BBC 169 (Dict. of Colour Standards). Wood — Canary Yellow ⅔ (Hort. Colour Chart).

Buds: 1-3 mm long.

*Internode length.*—5-25 cm.

*Thickness.*—3-15 mm.

*Strength.*—Brittle, bark is somewhat fibrous and strong; young branches moderately appressed sericeous, becoming glabrate with age; older branches glabrous, terete, with brown bark becoming fissured with shallow longitudinal groves, lenticels numerous, conspicuous, vascular tissues appearingto be divided into distinct bundles upon drying. Stipules, present, small, triangular.

Foliage:

*Shape.*—Lanceolate, the apex acuminate or somewhat cuspidate.

*Margin.*—Entire, somewhat undulating.

Arrangement on stems: Opposite.

Color:

*Young leaf.*—Above: Veronese Green 660 (Hort. Colour Chart).Below: Veronese Green 660/1 (Hort. Colour Chart). Old leaf: Above: Parsley Green 962 (Hort. Colour Chart). Below: Lettuce Green 861 (Hort Colour Chart).

Aspect: When young, appressed sericeous beneath and on veins and mid-rib above, glabrate beneath and glabrous above with age.

Venation: Feather-veined (11-13 primary veins).

Size: 6-16 cm. long. 2-7 cm. wide.

Petioles: Length — (15-30 mm). Color — Lettuce Green 861/3 (Hort. Colour Chart). Glands — (2-6) pairs. Angle to stem — (45 deg.-60 deg.). Sericeous when young, glabrous with age.

Reduced leaves: Often present.

Inflorescence: Axillary, appearing paniculate, length up to 30 cm. cymosely branched with ultimate division a 3-5 flowered umbel, bracts and bracteoles small, falling early, triangular to lanceolate 0.5-1.5 mm long, sparsely to densly appressed sericeous to tomentose.

Reduced leaves: Often present.

Flowers: Perfect.

Corolla:

*Petals.*—Five lobed, fimbriate, the four lateral petals reflexed between the sepals.

*Size.*—Lateral lobes with claw 1.0-1.8 mm long, limb 4-6 mm long, 3-5 mm broad, fimbriate, the posterior petal erect, the claw 1.5-3.0 mm long, the limb 7-8 mm long, 6-8 mm broad, fimbriate.

*Color.*—Rose-Ridgway plate 12 fading to white with age.

*Shape.*—Elliptic to obovate, with claw.

*Venation.*—Palmate.

*Aspect.*—Glabrous.

*Margin.*—Finely serrate.

Stamens: Numerous.

*Filaments.*—Thick, numerous, of uneven length, 2-4 mm long.

*Color.*—Yellow.

*Anthers.*—Numerous, large of uneven maturity, basifixed 1-1.3 mm long.

*Color.*—Yellow.

*Ovary.*—Single, 1-1.2 mm tall, densely sericeous.

*Pistils.*—Shorter than filaments. Stigma: inferior to anthers. Color: yellow.

*Sepals (calyx).*—Five, reintrant alternating with petals. tips embracing filaments and styles, the lobes ovate-lanceolate, 3 mm long densely sericeous. Tips: Outwardly curled. Color: Light green.

*Aspect.*—Densely sericeous. Length: 4 mm.

Pedicels: Appressed sericeous or densely tomento sericeous, 3-15 mm long.

Bracteoles: Densely tomento sericeous, 1-1.3 mm long.

Fruit: Unobserved to date.

| Character | *B. caapi* | DA VINE |
|---|---|---|
| Leaf size | (4.8–) 8.2-15.9 (–20.5) cm long × (2.5–) 3.5-7.7 (–11.5) cm wide | 9-14.7 cm long 3.5-5.8 cm. broad |
| Leaf shape | broadly ovate to ovate | ovate-elliptic to ovate-lanceolate |
| Leaf texture | coriaceous | chartaceous |
| Pedicel length | 7-11 mm | 3-15 mm |
| Pubescence on underside of young leaf | very sparsely appressed - sericeous to glabrate | densely appressed - sericeous, esp. along midrib |
| Pubescence on young branches | sparsely appressed - sericeous to glabrate | densely appressed - sericeous |
| Petal color | pale pink becoming pale yellow with age | rose, becoming white with age |
| Lateral petal size | limb 5.0-8.5 mm × 4.0-6.0 mm | limb 4.0-6.0 mm × 3.0-5.0 mm |
| Posterior petal size | limb 5.0-7.0 mm × 2.5-4.5 mm | limb 7.0-8.0 mm × 6.0-8.0 mm |

General observations: The plant appears to be seasonal in its flowering with flowering observed to occur from December through late March in Oahu, Hi. The plant parts are generally uniform in size throughout the plant; flower size and sizes of flowers parts are nearly identical as observed at Harold Lyon Arboretum, University of Hawaii, Oahu.

I claim:

1. The new and unique *Banisteriopsis caapi* plant substantially as described and illustrated.

* * * * *

US00PP05751C1

(12) REEXAMINATION CERTIFICATE (4307th)

United States Patent

Miller

(10) Number: US PP5,751 C1

(45) Certificate Issued: Apr. 17, 2001

(54) ***BANISTERIOPSIS CAAPI* (CV) 'DA VINE'**

(75) Inventor: Loren S. Miller, 1788 Oak Creek Dr., Apt. 407, Palo Alto, CA (US) 94303

(73) Assignee: Loren S. Miller, Palo Alto, CA (US)

Reexamination Request:
No. 90/005,307, Mar. 30, 1999

Reexamination Certificate for:

| | |
|---|---|
| Patent No.: | **P.P. 5,751** |
| Issued: | **Jun. 17, 1986** |
| Appl. No.: | **06/669,745** |
| Filed: | **Nov. 7, 1984** |

Related U.S. Application Data

(63) Continuation of application No. 06/266,114, filed on May 21, 1981, now abandoned.

(51) Int. Cl.[7] ..... A01H 5/00

(52) U.S. Cl. ..... Plt./226

(58) Field of Search ..... Plt./226, 395

(56) References Cited

PUBLICATIONS

Plants of Cultivation: *Banisteriopsis caapi,* Accessioned Specimen Sheet, The University of Michigan Herbarium (mounted Jan. 5, 1981). [Exhibit No. 1].

Plants of Cultivation: *Banisteriopsis caapi,* Field Museum of Natural History Herbarium Accession Sheet No. 1823910 (mounted Apr. 24, 1978). Exhibit No. 2.

Plants of Florida: *Banisteriopsis caapi,* Field Museum of Natural History Herbarium. [Exhibit No. 3].

Plants of Florida: *Banisteriosis caapi,* Field Museum of Natural History Herbarium Plowman #12973. [Exhibit No. 4].

Dobkin de Rios, Marlene, A Note on the Use of Ayahuasca Among Urban Mestizo Populations in the Peruvian Amazon, 72 Am. Anthropologist 1419–21 (1970). [Exhibit No. 5].

Dobkin de Rios, Marlene, Banisteriopsis in Witchcraft and Healing Activities in Iquitos, Peru, 24 Econ. Botany 296–99 (1970). [Exhibit No. 5].

Dobkin de Rios, Marlene, Ayahuasca—The Healing Vine, 27 Int'l J. Soc. Psychiatry 256–67 (1971).[Exhibit No. 6].

Dobkin de Rios, Marlene, The Wilderness of Mind: Sacred Plants in Cross–Cultural Perspective 69–73 (Sage Research Paper No. 90–039, 1976). [Exhibit No. 8].

Dobkin de Rios, Marlene, Visionary Vine: Psychedelic Healing in the Peruvian Amazon 38–47, 67–76, 88, 99–116, 129–40 (Chandler Pub. for Health Sciences, 1972). Exhibit No. 9.

Flores, Franklin Ayala & Walter H. Lewis, Drinking the South American Hallucinogenic Ayahuasca, 32 Econ. Botany 154 (1978). [Exhibit No. 10].

Hill, Albert F., Economic Botany: A Textbook of Useful Plants and Plant Products 283–84 (2d ed. 1952). [Exhibit No. 11].

Rivier, Laurent & Jan–Erik Lindgren, "Ayahuasca," the South American Hallucinogenic Drink: An Ethnobotanical and Chemical Investigation, 26 Econ. Botany 101–03, 109, 117 (1972). [Exhibit No. 12].

Schultes, Richard Evans & Albert Hofmann, *The Botany and Chemistry of Hallucinogens* 163–81 (American Lecture Series No. 1025, 1980). [Exhibit No. 13].

Briggs, D. & S.M. Walters, *Plant Variation and Evolution* 93–94 (1969). [Exhibit No. 14].

Stace, Clive A., *Plant Taxonomy and Biosystematics* 186–90 (1980). [Exhibit No. 15].

Stebbins, G. Ledyard, Jr., *Variation and Evolution in Plants* 72–6 (1950). [Exhibit No. 16].

Declaration by William R. Anderson, Director of the herbarium at the University of Michigan. [Exhibit No. 17].

Declaration by Christine Niezgoda, Collections Manager of the herbarium of the Field Museum in Chicago. [Exhibit No. 18].

Declaration by Antonio Jacanamijoy, General Coordinator for the Coordinating Body of Indigenous Organizations of the Amazon Basin (COICA). [Exhibit No. 19].

Gates, Bronwen, Banisteriopsis, Diplopterys (Malpighiaceae) 1, 112–14, 117 (Flora Neotropica Monograph No. 30, 1982). [Exhibit No. 20].

*Primary Examiner*—Howard J. Locker

(57) ABSTRACT

A new and distinct *Banisteriopsis caapi* plant named 'Da Vine' which is particularly characterized by the rose color of its flower petals which fade with age to near white, and its medicinal properties.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim 1 is confirmed.

* * * * *